United States Patent
Hutten

(10) Patent No.: US 6,519,494 B1
(45) Date of Patent: Feb. 11, 2003

(54) RATE-ADAPTIVE CARDIAC PACEMAKER

(75) Inventor: Helmut Hutten, Graz (AT)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/642,449

(22) Filed: Aug. 18, 2000

(30) Foreign Application Priority Data

Aug. 20, 1999 (DE) .......................... 199 40 952

(51) Int. Cl.⁷ ................................ A61N 1/08
(52) U.S. Cl. ..................................... 607/17
(58) Field of Search ................. 600/509, 527, 600/531, 533; 607/4, 5, 6, 7, 9, 11, 17, 18, 19, 20, 62, 119

(56) References Cited

U.S. PATENT DOCUMENTS

| | | | |
|---|---|---|---|
| 3,593,718 A | | 7/1971 | Krasner et al. ............. 128/419 |
| 4,884,576 A | | 12/1989 | Alt ............................. 128/419 |
| 5,514,162 A | * | 5/1996 | Bornzin et al. .............. 607/19 |
| 5,782,884 A | * | 7/1998 | Stotts et al. ................ 607/17 |
| 5,792,200 A | | 8/1998 | Brewer ........................ 607/20 |
| 5,891,175 A | * | 4/1999 | Walmsley et al. ........... 607/17 |
| 5,964,788 A | * | 10/1999 | Greenhut .................... 607/17 |
| 6,128,534 A | * | 10/2000 | Park et al. .................... 607/17 |

FOREIGN PATENT DOCUMENTS

| | | |
|---|---|---|
| DE | 44 47 447 | 7/1996 |
| DE | 196 09 409 | 9/1997 |
| DE | 198 59 653 | 6/2000 |
| EP | 0 089 014 | 9/1983 |
| EP | 0 151 689 | 8/1985 |
| EP | 0 249 818 A1 | 12/1987 |
| EP | 0 249 818 | 12/1987 |
| EP | 0 151 689 B1 | 12/1990 |
| EP | 0 449 401 A2 | 10/1991 |
| EP | 0 502 918 | 9/1992 |
| EP | 0 502 918 B1 | 5/1994 |
| EP | 0 804 939 | 11/1997 |
| EP | 0 804 941 | 11/1997 |

* cited by examiner

Primary Examiner—Jeffrey R. Jastrzab
Assistant Examiner—Frances P. Oropeza
(74) Attorney, Agent, or Firm—Christie, Parker & Hale, LLP

(57) ABSTRACT

A rate-adaptive cardiac pacemaker (1) comprising sensor means (1a through 4) for detecting a measurement parameter (RR) in the body of a patient, which is related to the circulation function, stimulation means (8, 2) for producing and outputting stimulation pulses to the heart (H) of the patient and rate control means (5) for establishing the rate of the stimulation pulses (SRabs) in dependence on the measurement parameter which is related to the circulation function, wherein the rate control means have an adjusting device (7) which is adapted for absolute value adjustment of a lower limit rate (SRmin) of the stimulation pulses and/or the configuration of a rate control characteristic curve (6a) describing the dependency of the rate of the stimulation pulses on the measurement parameter, in a stable state of low physical load.

15 Claims, 2 Drawing Sheets

RATE-ADAPTIVE CARDIAC PACEMAKER

CROSS-REFERENCE TO RELATED APPLICATIONS

This application claims priority on German Application No. 19940952.8, filed Aug. 20, 1999.

BACKGROUND OF THE INVENTION

The invention concerns a rate-adaptive cardiac pacemaker comprising sensor means for detecting at least one measurement parameter in the body of the patient, which is related to the circulation function, stimulation means for producing and outputting stimulation pulses to the heart of the patient, and rate control means which are connected at the input side to the sensor means and at the output side to the stimulation means, for controlling the rate of the stimulation pulses in dependence on the measurement parameter which is related to the circulation function.

Frequency- or rate-adaptive cardiac pacemakers are known in a wide range of different forms and have long been in clinical use. As they can react to changes in the physiological needs of the patient with changes in the stimulation frequency, it is possible to effectively take account of changing patient loading and strain states.

The design of a rate-adaptive pacemaker can be based on very different approaches in terms of control and regulation procedures. Basically, it is all the more promising in terms of success, the more extensively it takes advantage of the physiological interrelationships between loading and pulse rate in the patient with a sound heart.

Particularly advantageous from that point of view are sinus node-controlled units which directly sense the electrical sinus node or atrium activity. Those atrium-synchronous pacemakers are regularly used in connection with syndromes involving atrio-ventricular conduction interference with an intact sinus node function. In such cases the absolute value of the stimulation rate is predetermined at any time directly by the body-specific stimulation system under the guidance of the central nervous system (CNS).

DESCRIPTION OF THE RELATED ART

Matters are different in regard to frequency-adaptive pacemakers which can be used in the therapy of syndromes involving disturbances in the sinus node function: Pacemakers of that kind use in various ways items of sensor information relating to the physiological needs of the patient and/or the physical activity of the patient. Those measurement values and the changes in the stimulation frequency, which are ascertained therefrom, are however basically relative in nature—see for example U.S. Pat. No. 3,593,718 which gives one of the first descriptions of a (respiration-controlled) rate-adaptive pacemaker. In other words, pacemakers of that kind do not involve information about the physiologically correct absolute value of the stimulation frequency. Nonetheless, the function thereof, on the basis of that relative stimulation frequency parameter, can be satisfactory in many situations of use as maladjustments of the absolute stimulation frequency are compensated by the body-specific regulation of the heart beat volume. Compensation in respect of rate maladjustments by the heart beat volume however represents an ongoing additional loading and strain on the patient and in addition naturally involves certain limits in regard to patients with reduced volume adaption capability.

For example U.S. Pat. No. 4,884,576 proposes patient-specific calibration of the characteristic curve which serves to determine the stimulation rate, between a lower and an upper limit rate, in which case specifically the long-term average value of the respiration signal is intended to serve to establish the configuration of the characteristic curve and optionally additional signals are intended to serve for displacement within the fixedly predetermined stimulation frequency band.

BRIEF SUMMARY OF THE INVENTION

The object of the present invention is to provide a cardiac pacemaker of the general kind set forth, in which maladjustments of the absolute stimulation rate over the entire relevant adjustment range are avoided.

That object is attained by a cardiac pacemaker having the features recited in claim 1.

The invention embraces the concept of providing the pacemaker with means for obtaining sensor information about the physiologically correct absolute value of the stimulation frequency. As natural heart rate information is not available for the pacemaker types which are involved here, the invention further involves the notion of replacing same by sensor information about another available parameter which is regulated in terms of central nervous system. An advantageous starting point in this respect is the central-nervous coupling of respiration and circulation activity, in which in particular heart rate, heart beat volume and vasomotor system (here in particular the vessel resistance) are of significance as circulation-relevant parameters. As the pacemaker rate is intended to reproduce the physiological heart rate as accurately as possible, the invention in particular embraces the notion of obtaining a physiologically correct absolute value for the stimulation rate, by means of suitable processing of a respiration signal.

In the case of a healthy human body, close coupling occurs between respiration activity and base heart rate within given frequency relationships primarily in rest phases, especially while asleep at night. The frequency relationship which occurs can depend on whether the patient is active in a sport context. As a general trend for example for endurance athletes the heart/respiration frequency relationship is about 3, while for people who are less active in a sporting sense it is about 4.

Advantageously, by virtue of the ease of technical implementability, provided for the detection of respiration signals is an impedance sensor which is modified in regard to signal evaluation (impedance pneumograph) which has long been known as such and which is described for pacemakers for example in EP 0 151 689 B1 or EP 0 249 818 A1. Measurement of the respiration rate can be effected either alternatively or jointly by measurement of the intrathoracal and/or the intracardial impedance. If both intrathoracal and also intracardial impedance are measured, then those measurements can be utilized for mutual signal cleaning.

In consideration of the above-mentioned relationships, firstly (nighttime) rest phases are to be detected by the pacemaker. They can be recognized by virtue of the information from other sensors, for example by the detection of rapid eye movement phases. EP 0 502 918 B1 makes use of activity sensor data for detection of rest or sleep phases.

It is particularly desirable however for the respiration rate sensor which is provided to obtain the relevant measurement data also to be used for the detection of nighttime rest phases. Sleep phases can thereby generally be detected on the basis of a given level and in particular a given stability of the respiration rate.

The rate adaptation algorithm of the cardiac pacemaker can be retained independently of changes in the base stimulation rate. The rate ascertained on the basis of the algorithm—so-to-speak the dynamic component—is then displaced towards higher or lower rates, in accordance with an offset which is ascertained from the respiration signal— the static component. It is then to be expected that the average stimulation frequency also changes to a similar degree to the base stimulation rate.

On the other hand there is the possibility of varying the rate adaptation algorithm in such a way that, upon changes in the base stimulation rate, the original maximum rate is still attained. For that purpose the gradient of the rate control characteristic curve must be raised or reduced in inverse proportion to changes in the base stimulation rate.

The invention can be used to particular advantage in relation to cardiac pacemakers which, for dynamic rate adaptation purposes, evaluate complex curve shapes such as the variation in respect of time of the intracardial impedance, the ventricular evoked response (VER) or the monophasic action potential (MAP). When evaluating such curves for the purposes of deriving rate control signals, the difficulty is frequently encountered that a reference curve configuration which is to be correlated to the base stimulation rate of the cardiac pacemaker has to be found for the resting patient. In regard to such cardiac pacemakers, the invention permits simultaneous detection of a reference curve configuration and the associated base stimulation rate.

A further development of the invention in regard to such cardiac pacemakers which evaluate complex curve shapes of cardiac activity signals provides that a medium stable load state is also detected on the basis of respiration activity (that is to say the rate thereof=respiration frequency and stroke capacity=respiration volume) in order to be able to record a reference curve for medium load states. More specifically as the coupling between respiration and heart rates disappears with increasing load, it is no longer possible to absolutely determine a heart rate at medium loads solely on the basis of the respiration rate and respiration rate and stroke capacity have to be detected for the purposes of detecting the load state. It will be noted that in that respect a further support location is also to be obtained in order to define the parameters of the rate adaptation algorithm and complete auto-calibration of the rate adaptation algorithm is made possible solely by means of a respiration sensor.

BRIEF DESCRIPTION OF THE DRAWINGS

Advantageous developments of the invention are moreover characterized in the appendant claims and are set forth in greater detail hereinafter in the course of the description of preferred embodiments of the invention with respect to the accompanying drawings in which:

DETAILED DESCRIPTION OF THE INVENTION

Figure 1:
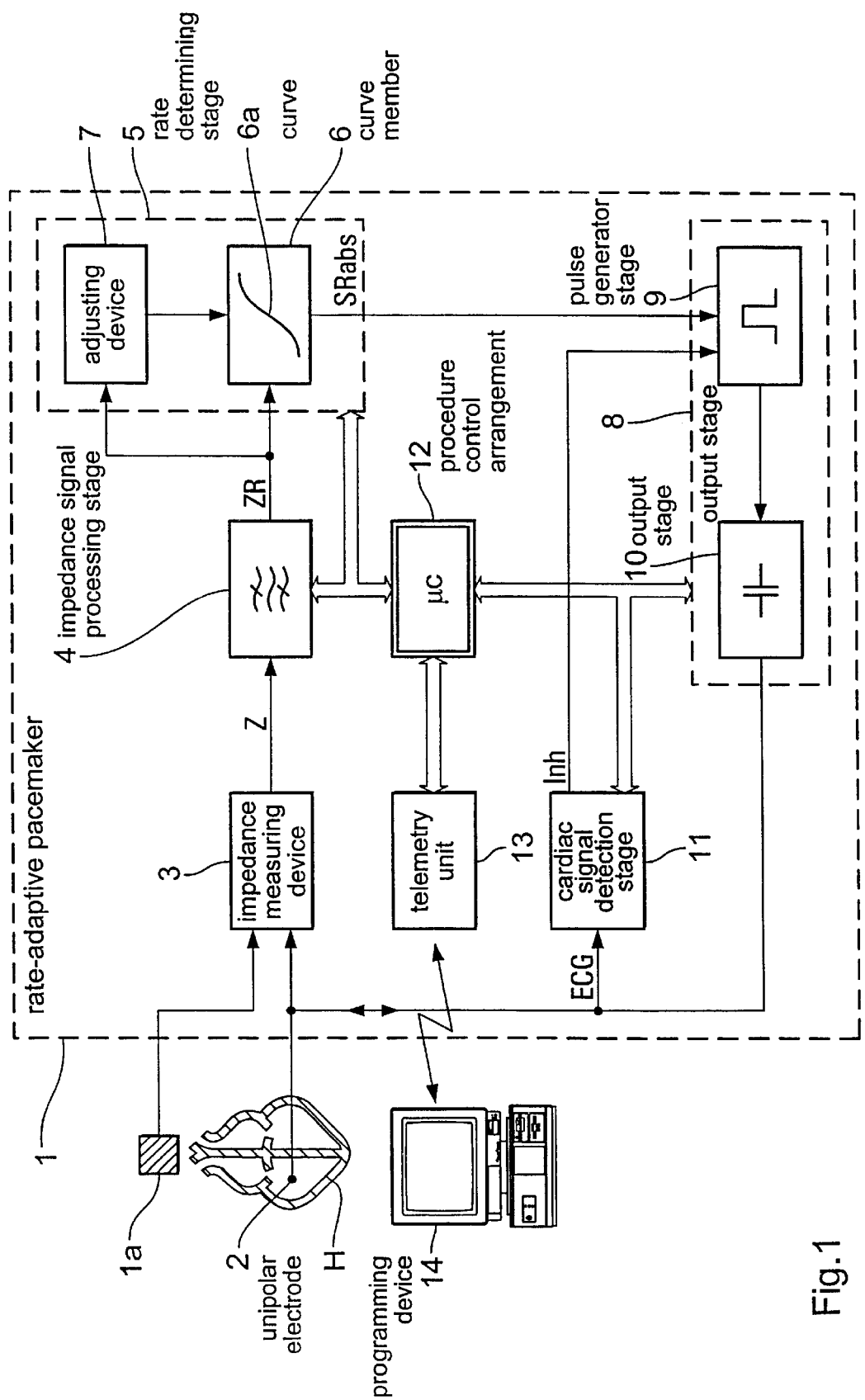
FIG. 1 is a functional block circuit diagram of a cardiac pacemaker in accordance with a preferred embodiment of the invention.

FIG. 1 shows a schematic functional block circuit diagram illustrating only the components which are important for describing the invention, a pacemaker arrangement with a rate-adaptive pacemaker 1.

The pacemaker 1 includes an impedance measuring device 3—which is known as such—and which is connected at the input side to a housing electrode 1a and a unipolar electrode 2 in the right ventricle of a heart H and which detects the impedance Z of the measurement section. Measurement is implemented by the electrode 2 being supplied with a (non-stimulating) measurement voltage at a clock frequency of some ten to about 100 Hz and by the current between the electrodes 1a and 2 being detected at predetermined time intervals within a fixedly preprogrammed time range. The impedance Z is the quotient of measurement voltage and current. Connected on the output side of the measurement device 3 is an impedance signal processing stage 4 with band pass filter properties for filtering out higher-frequency changes in impedance which are not caused by respiration, and for compensating for zero line drift, which produces an output signal ZR reflecting the respiration rate.

The output signal ZR of the signal processing stage 4 is fed to a rate determining device 5 which outputs a rate control signal SRabs which establishes the absolute value of the adaptive stimulation rate.

The rate determining device 5 has a characteristic curve member 6 which associates with each value of the respiration rate signal ZR, by means of a characteristic curve 6a, a value of the adaptive stimulation rate SRabs. The characteristic curve is periodically optimized by a characteristic curve adjusting device 7 during operation of the cardiac pacemaker, while (optionally) in each case the permissible range of variation in the stimulation rate SRabs between a base rate SRmin as a lower limit value and a maximum stimulation rate SRmax as an upper limit value is also freshly determined. Connected to the output side of the rate determining device 5 is a pulse generating and output stage 8 which is designed in the usual manner and which has a pulse generating stage 9 and an output stage 10 which is connected to the output thereof and which is connected to the electrode 2 (which in accordance with the foregoing serves simultaneously as a measurement and stimulation electrode), for the output of a stimulation pulse. The pulse generating and output stage 8 is connected by way of a further control input to the output of a cardiac signal detection stage 11 which by way of the electrode 2 takes off an intracardial electrocardiogram (ECG) at the heart and possibly derives therefrom an inhibition signal Inh by which the output of a stimulation pulse can be inhibited, in the event of an adequate natural frequency.

For the purposes of controlling the general pacemaker functions and for implementing the impedance measurement and processing procedures, there is a procedure control arrangement (controller) 12 which is in databus communication with the other pacemaker components and a telemetry unit 13 by way of which data exchange can be effected in per se known manner with an external evaluation and programming device 14.

Figure 2:
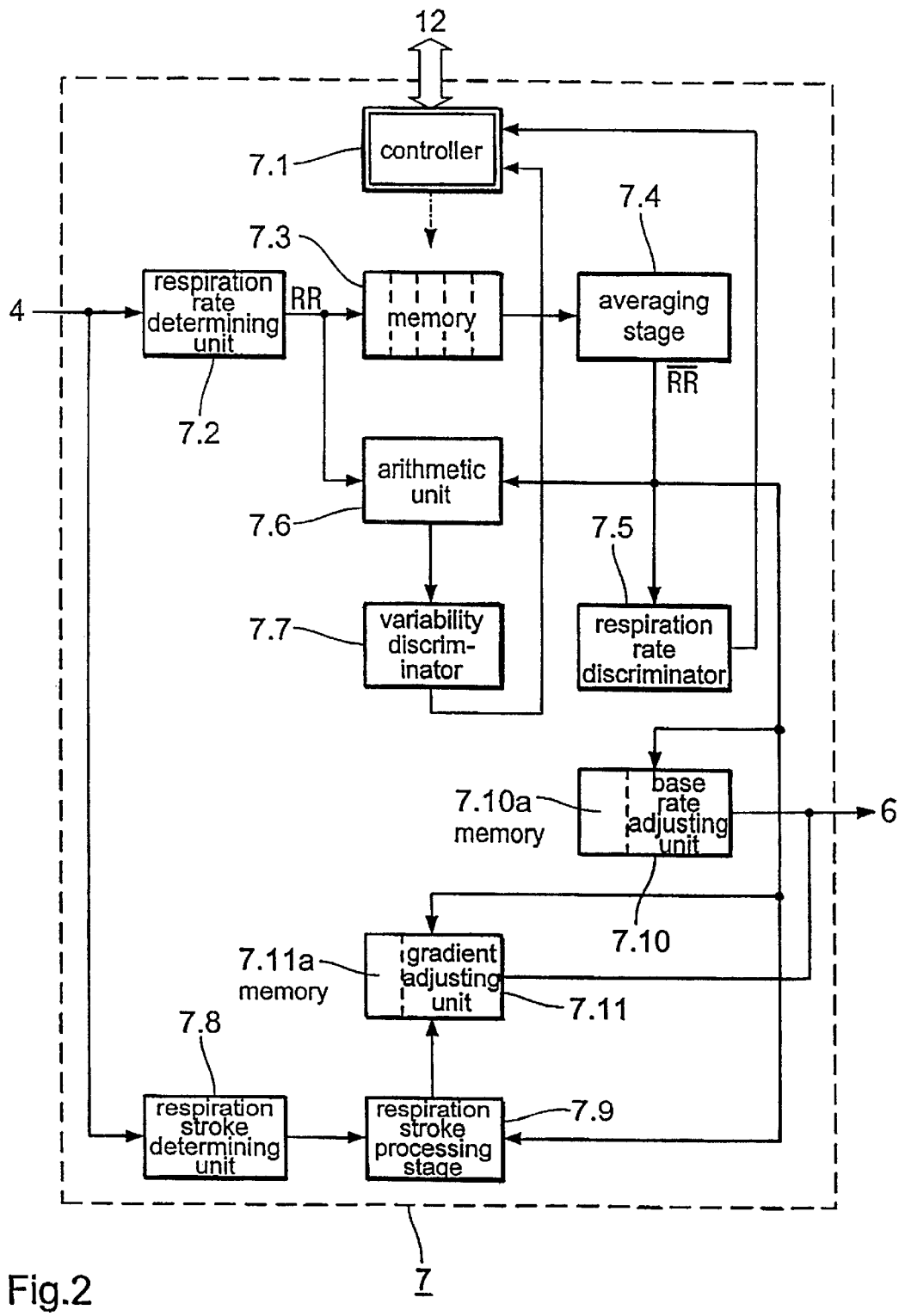
FIG. 2 is a functional block circuit diagram of an embodiment of the characteristic curve adjusting device of the pacemaker shown in FIG. 1.

FIG. 2 is a functional block circuit diagram showing the components of a characteristic curve adjusting device 7 of the pacemaker 1, which are essential for carrying the invention into effect. It is to be observed in this respect that calibration of a sensor-aided rate-adaptive pacemaker as such is something that is familiar to the man skilled in the art and the corresponding basic functions will not be described in greater detail herein. The man skilled in the art assumes moreover that the described functions can be at least partially implemented in software terms in a modern pacemaker.

The characteristic curve adjusting device 7 includes an internal procedure control arrangement or controller 7.1 which is connected on the one hand by way of a databus connection to the controller 12 and specifically to the time base thereof and on the other hand (by way of control connections which are not individually shown) to the components set out hereinafter, and controls execution of the steps described hereinafter, in a manner which is matched to the general pacemaker operation.

It further includes a respiration rate determining unit 7.2 connected at the input side to the impedance signal processing stage 4 (FIG. 1) and a respiration rate store or memory 7.3 connected downstream of the respiration rate determining unit 7.2 and—respectively connected on the input side to the memory 7.3—an averaging stage 7.4, a respiration rate discriminator 7.5 and an arithmetic unit 7.6 additionally connected to the averaging stage 7.4, for executing various calculations in regard to the respiration rate, as well as a variability discriminator 7.7 which is connected to the arithmetic unit 7.6.

The characteristic curve adjusting device 7 also includes a respiration stroke determining unit 7.8 which is also connected at the input side to the signal processing stage 4 and a respiration stroke processing stage 7.9 disposed on the output side of the respiration stroke determining unit 7.8, and also a base rate adjusting unit 7.10 with associated ratio store or memory 7.10a and a gradient adjusting unit 7.11 with associated characteristic curve shape store or memory 7.11a, which are connected on the output side to the characteristic member 6. The base rate adjusting unit 7.10 is also connected on the input side to the output of the averaging stage 7.4 and the gradient adjusting unit 7.11, besides same, is additionally connected to the output of the respiration stroke processing stage 7.9.

Adjustment of the rate control characteristic curve is effected by means of those components in the following preferred fashion.

Firstly, detection of a nighttime rest phase is effected on the basis of the association of the respiration rate with a given range of values and the fulfillment of a given stability criterion. If the controller 12 has a real time clock, such a detection procedure can be triggered at given clock times or also simply at predetermined time intervals by means of the internal controller 7.1. Thereupon, for a number of breaths which is determined by the capacity of the respiration rate memory 7.3, the instantaneous breathing frequency (respiration rate) is continuously determined, stored and averaged by the stages 7.2 through 7.4. In the respiration rate discriminator, the average value is subjected to a discrimination operation in regard to the association with a predetermined frequency range and in addition, in the arithmetic unit 7.6 and the variability discriminator 7.7, the variability of the frequency of the predetermined number of breaths is determined and checked to see whether it falls below a predetermined threshold value.

The criteria for the existence of a sleep phase are the occurrence of a group of between 4 and 8 breaths with a rate variability of not over 10% and a rate within a range of between 15 and 25 per minute. The fulfillment of the criteria is checked within a test period which is programmed in the controller 7.1 and the test is terminated either when both criteria are satisfied or after expiry of the test period. If the result is positive the steps described hereinafter will be executed while if the outcome is negative the currently applicable rate control characteristic curve is retained for the time being.

If a sleep phase was detected, the averaged respiration rate is passed to the base rate adjusting unit 7.10 and is there multiplied by a factor of between 2.5 and 4.5 which is stored in the associated memory 7.10a, in order thereby to obtain the current base rate. Advantageously, the memory 7.10a can be programmable by the physician. In that way it is possible to select a value corresponding to the sporting condition of the patient, in which respect lower values are selected in the case of patients who are involved in endurance sport than in the case of inactive patients. (Basically—for example in the case of an additionally activity-controlled pacemaker with histogram functions—there is also the option of making the factor adaptive by virtue of the fact that in regard to patients in respect of whom marked physical activity over long periods of time is detected, it is automatically set lower or is reduced, in comparison with rather inactive patients.)

The configuration of the characteristic curve can either be left unchanged upon a change in the base rate (which also results in an offset of the maximum rate) or—also initiated by the controller 7.1—a configurational adaptation procedure is implemented straight-away by the gradient adjusting unit 7.11, with access to the reserve characteristic curves stored in the characteristic curve shape memory 7.11a, to the effect that the previous maximum rate is retained. Addressing of the stored characteristic curves is effected on the basis of the output value of the base rate adjusting unit 7.10. Independently thereof, setting or re-adjustment of the characteristic curve configuration can be effected in a phase of medium patient load or stress, on the basis of common processing of respiration rate and stroke. The presence of such a phase is detected, in a similar manner to the above-described detection of a rest phase, on the basis of a given range association and the fulfillment of a variability criterion. In addition (although this is not apparent from the Figure) it may also be desirable to check for the fulfillment of predetermined range and variability criteria for the respiration stroke movement.

If a state of stable medium load has been detected, then the respiration stroke movement which is ascertained in parallel with the respiration rate in the respiration stroke determining unit 7.8 and the associated respiration frequency signals from the averaging stage 7.4 or the arithmetic unit 7.6 are subjected to common processing in accordance with a predetermined algorithm in the respiration stroke processing stage 7.9. The details of such an algorithm however do not form part of the present invention and are therefore not described herein.

The invention is not limited in terms of the implementation thereof to the preferred embodiments set forth hereinbefore. On the contrary a number of alternative configurations are possible, which make use of the illustrated structure even in configurations of a different kind.

Thus the invention, in the sense of a qualified dual-sensor concept, can also be used in particular in relation to pacemakers which have a further sensor for a load-dependent parameter with a rate control characteristic curve which is specific to that sensor. In that connection it permits the physiologically correct association of a base rate or characteristic curve starting point with the given characteristic curve configuration and thus permits conversion of the relative rate control mentioned in the opening part of this description into an absolute value control. In the last-mentioned alternative configuration with additional respiration stroke evaluation in a medium load state, verification of the characteristic curve configuration then additionally becomes a possibility, which further increases the physiological quality of the control. Furthermore use of the parameter which in given physical states closely correlates with the heart rate—for example the respiration rate and possibly also the respiration stroke—is not limited to control of the stimulation rate, but it can also be utilized in a dual-chamber pacemaker in a similar manner for controlling the AV-interval.

What is claimed is:

1. A rate-adaptive cardiac pacemaker comprising:
   sensor means having an output, the sensor means being designed for detecting at least one measurement parameter in the body of a patient related to the circulation function;
   stimulation means having an input, the stimulation means being designed for producing and outputting stimulation pulses at a stimulation control rate to the heart of the patient; and
   rate control means connected between the sensor means output and the stimulation means input, for controlling the stimulation control rate in a dependence on the at least one measurement parameter, the rate control means further including an adjusting device:
   the adjusting device:
      adapted to alter the dependence of the stimulation control rate on the at least one measurement parameter by applying at least one adjusting parameter to the dependence, wherein the at least one adjusting parameter is based on the physical condition of the patient and wherein the dependence is adjusted during a stable state of low or medium physical load on the body, and the adjusting device further including:
         state detecting means for detecting the state of physical load on the body by comparing a property of the at least one measurement parameter with a predetermined criteria.

2. A rate-adaptive cardiac pacemaker as set forth in claim 1 wherein the rate control means are adapted such that they vary a dynamic component of the stimulation control rate in dependence on one of the at least one measurement parameters which is related to the current physical load of the body of the patient, in relation to a static component which depends on the adjusting parameter, which is ascertained during a rest phase.

3. A rate-adaptive cardiac pacemaker as set forth in claim 1 wherein the state detecting means have means for associating a current value of the at least one measurement parameter with a predetermined range of values.

4. A rate-adaptive cardiac pacemaker as set forth in claim 1 wherein the state detecting means have means for ascertaining the variability of the at least one measurement parameter and for comparing the variability of the at least one measurement parameter with a predetermined limit value.

5. A rate-adaptive cardiac pacemaker as set forth in claim 1 wherein the at least one adjusting parameter is utilized to adjust an absolute value of a lower limit rate of the stimulation pulses.

6. A rate-adaptive cardiac pacemaker as set forth in claim 1 wherein the at least one adjusting parameter is utilized as an offset for a rate characteristic curve which describes the dependency of the stimulation control rate on the at least one measurement parameter.

7. A rate-adaptive cardiac pacemaker as set forth in claim 1 wherein the adjusting device has adjusting means for adjusting a lower limit rate and/or at least one portion of a rate control characteristic curve in accordance with a predetermined relationship, wherein the adjusting means are activated upon detection of a stable state of low load.

8. A rate-adaptive cardiac pacemaker as set forth in claim 1 wherein the at least one measurement parameter is a respiration rate and the sensor means are adapted to determine the respiration rate on the basis of measurements of an intrathoracal impedance.

9. A rate-adaptive cardiac pacemaker as set forth in claim 1 wherein the at least one measurement parameter is a respiration rate and the sensor means are adapted to determine the respiration rate on the basis of measurements of an intracardial impedance.

10. A rate-adaptive cardiac pacemaker as set forth in claim 8 or claim 9 wherein the adjusting device is designed such that a lower limit rate and/or the stimulation control rate are in an adjustable relationship with the respiration rate.

11. A rate-adaptive cardiac pacemaker as set forth in claim 10 wherein the adjusting device is designed such that the lower limit rate and/or the stimulation control rate are in an adjustable relationship with a longer-term means value of the respiration rate.

12. A rate-adaptive cardiac pacemaker as set forth in claim 1 wherein the adjusting device is adapted for the additional calibration of a rate control characteristic curve in a stable state of medium load.

13. A rate-adaptive cardiac pacemaker as set forth in claim 9 wherein the sensor means are adapted to detect a respiration stroke movement and the state detecting means and/or the adjusting means are adapted to evaluate the respiration stroke movement in the stable state of medium load.

14. A rate-adaptive cardiac pacemaker as set forth in claim 1 further comprising second sensing means for detecting a further activity- or load-dependent measurement parameter, and wherein the adjusting device is adapted to adjust a rate control characteristic curve in dependence on the further measurement parameter.

15. A rate-adaptive cardiac pacemaker as set forth in claim 1 further comprising second sensing means adapted to sense a load-dependent measurement parameter in a cardiac activity signal.

* * * * *